United States Patent
Yamashita et al.

(10) Patent No.: US 6,597,001 B1
(45) Date of Patent: Jul. 22, 2003

(54) METHOD OF ELECTRON-BEAM EXPOSURE AND MASK AND ELECTRON-BEAM EXPOSURE SYSTEM USED THEREIN

(75) Inventors: Hiroshi Yamashita, Tokyo (JP); Hideo Kobinata, Tokyo (JP)

(73) Assignee: NEC Electronics Corporation, Kanagawa (JP)

( * ) Notice: Subject to any disclaimer, the term of this patent is extended or adjusted under 35 U.S.C. 154(b) by 0 days.

(21) Appl. No.: 09/712,220

(22) Filed: Nov. 15, 2000

(30) Foreign Application Priority Data

Nov. 17, 1999 (JP) .......................... 11-327271

(51) Int. Cl.[7] .................... G01J 1/00; G01N 21/00; G01N 23/00
(52) U.S. Cl. ................ 250/491.1; 250/492.21; 250/492.22
(58) Field of Search .............. 250/492.21, 492.22, 250/306, 492.23, 491.1

(56) References Cited

U.S. PATENT DOCUMENTS

| 5,130,213 A | * | 7/1992 | Berger et al. | ........... 250/492.2 |
| 5,451,487 A | * | 9/1995 | Abe et al. | ........... 250/492.2 |
| 5,789,119 A | * | 8/1998 | Okino | ........... 430/5 |

FOREIGN PATENT DOCUMENTS

| JP | 63-155724 | 6/1988 |
| JP | 63-308919 | 12/1988 |
| JP | 3-101214 | 4/1991 |
| JP | 5-175108 | 7/1993 |
| JP | 5-335221 | 12/1993 |
| JP | 6-151286 | 5/1994 |
| JP | 7-240358 | 9/1995 |
| JP | 7-297094 | 11/1995 |
| JP | 10-64780 | 3/1998 |
| JP | 10-256135 | 9/1998 |
| JP | 11-176720 | 7/1999 |
| JP | 11-186151 | 7/1999 |

OTHER PUBLICATIONS

Watson et al., "A Background Dose Proximity Effect Correction Technique for Scattering with Angular Limitation Projection Electron Lithography Implemented in Hardware ", J. vac. Sci. Technol. B, vol. 13 No. 6, Nov./Dec. 1995, American Vacuum Society, pp. 2504–2507.

* cited by examiner

Primary Examiner—John R. Lee
Assistant Examiner—Kalimah Fernandez
(74) Attorney, Agent, or Firm—Young & Thompson

(57) ABSTRACT

An electron-beam exposure method of segmented mask-pattern transfer type wherein a prescribed pattern is segmented into a plurality of divisions so as to form a segmented pattern in every division and exposure is made through every division one after another, so that the projection of the whole of the prescribed pattern is accomplished. The method includes the steps of carrying out the exposure through every division and transcribing a segmented pattern thereon one after another. The method also includes the steps of carrying out the correction exposure for every projection region of the segmented patterns one after another with a defocused beam of the inverse pattern of the respective segmented patterns, and thereby the proximity effect caused by the pattern exposure is corrected.

6 Claims, 9 Drawing Sheets

(a)

(b)

(a)

(b)

(c)

(d)

(e)

METHOD OF ELECTRON-BEAM EXPOSURE AND MASK AND ELECTRON-BEAM EXPOSURE SYSTEM USED THEREIN

BACKGROUND OF THE INVENTION

1. Field of the Invention

The present invention relates to a method of electron-beam exposure and a mask as well as an electron-beam exposure system used therein, and more particularly to an electron-beam exposure method of segmented mask-pattern transfer type that is employed to manufacture a semiconductor device and especially suited for the proximity effect correction and a mask as well as an electron-beam exposure system used therein.

2. Description of the Related Art

In the electron-beam exposure that is performed in the step of lithography for manufacturing a semiconductor device, the proximity effect caused by scattered electrons within a substrate and its coating resist layer strongly affects the linewidth accuracy of projection patterns. For instance, in closely spaced line and space patterns, electrons that enter into an exposed section may be severely scattered (back-scattering) within a substrate, and a resist in an adjacent unexposed section may be subjected to exposure (background exposure) by such back-scattering electrons. As a result, edge sections and central section of one pattern become displaying different distributions of deposited energy, as shown in FIG. 4, and a prescribed pattern that is set at an appropriate threshold level of energy becomes unobtainable when the resist is developed (particularly in edge sections). This highlights the fact that the proximity effect correction is one of the essential techniques in the art.

As the actual method of the proximity effect correction, there are known the dose compensation method in which, at the time of the pattern exposure, the optimum dose is appropriately chosen depending on the dose of background exposure and the GHOST exposure method wherein correction exposure is made so as to bring the dose of the background exposure to a constant level in all regions where pattern exposure is carried out.

In the cell projection method and the variable-shaped beam exposure method both of which are currently widely used methods of electron-beam exposure, in order to make the proximity effect correction according to the dose compensation method, the self-consistent method using the exposure intensity distribution (EID) function, the pattern density method or the like has been presently employed, any of which requires complicated calculations. In consequence, a lengthy time is required for the data processing, and besides for every different pattern to transfer, another set of complicated calculations of this sort must be made.

The GHOST method is a technique in which, after the primary pattern (the positive pattern) for exposure is subjected to exposure, weak correction exposure (GHOST exposure) is performed with the beam that is formed by defocusing the inverse pattern of the positive pattern over the back-scattering range, and thereby the proximity effect that may be brought about through back-scattering of the incident electrons for the positive pattern exposure is corrected. FIG. 5 is a diagram in explaining the principle of proximity effect correction according to the offset GHOST method that is a sort of the GHOST method, which shows schematically the distribution of deposited energy by the electron-beam exposure. FIG. 5(a) presents the distribution of deposited energy with the primary pattern of line and space (1/1) and FIG. 5(b), the distribution of deposited energy by the correction exposure with the beam that is formed by defocusing the inverse pattern over the back-scattering range, while FIG. 5(c) illustrates the distribution of deposited energy in the case the correction exposure to provide such a distribution of deposited energy as shown in FIG. 5(b) is applied to the exposed region of FIG. 5(a). In the drawings, the energy of forward-scattering electrons is set to be 1, and η and βb represent the back-scattering coefficient and the back-scattering range, respectively. By making the proximity effect correction according to the GHOST method, the dose of background exposure can be brought to a constant level as shown in FIG. 5(c). Consequently, the distribution of deposited energy can become uniform throughout and the linewidth accuracy of the pattern, improved.

However, to apply the GHOST method of this sort to the cell projection lithography method or the variable-shaped beam exposure method, the exposure intensity must be none the less calculated using the EID function or the like. In addition, since complicated calculations are necessary for formation of the inverse pattern, considerable time is required for data processing. The projection of the inverse pattern obtained in this way also takes time. These factors all contribute to marked reduction of the throughput Meanwhile, as a novel method of electron-beam exposure to replace the cell projection lithography method and the variable-shaped beam exposure method, an electron-beam exposure method of segmented mask-pattern transfer type has been recently proposed. This electron-beam exposure method of segmented mask-pattern transfer type is a method wherein a prescribed primary pattern for exposure is segmented into a plurality of divisions and every said divisions is subjected to exposure one by one till the whole of this prescribed primary pattern is transferred. Although the prescribed primary pattern is segmented into a plurality of divisions, this electron-beam exposure method of segmented mask-pattern transfer type uses a mask onto which the whole segmented portions of the prescribed pattern of one chip are formed in all. In this respect, the electron-beam exposure method of segmented mask-pattern transfer type is altogether different from the variable-shaped beam exposure method wherein a pattern that is to be formed is not actually formed onto the mask but processed as soft data or the cell projection lithography method which employs a mask onto which only repeated parts of a prescribed pattern is formed.

This electron-beam exposure method of segmented mask-pattern transfer type is explained well in the section of the prior art in Japanese Patent Application Laid-out No. 176720/1999 with reference to FIG. 2 in the publication. On the basis of this description, the electron-beam exposure method of segmented mask-pattern transfer type is described below.

FIG. 6 is a schematic view in explaining the electron-beam exposure method of segmented mask-pattern transfer type. In FIG. 6, referential numeral 100 indicates a mask; 100a, a division on the mask; 100b, a demarcation region between divisions 100a; 110, a substrate coated with a resist, such as a wafer; 110a, a region for one die (one chip) on the substrate 110; 110b, a region for projection on the substrate 110, each corresponding to a division 100a; AX, an optical axis of an optical system of charged particle beam; EB, a charged particle beam and CO, a crossover point of the optical system of charged particle beam.

On the mask 100, being separated by a demarcation region 100b without a pattern, there are present numerous divisions 100a each of which is provided, on a membrane, a pattern to be transferred onto the substrate 110. Further, a support structure in the form of a grid is set over the demarcation region 100b, protecting the membrane thermally and mechanically. The mask 100 herein is a scattering membrane mask wherein, on a membrane, for example, a silicon nitride film with a thickness of 100 nm or so, there are formed electron-beam scatterer patterns made of, for example, tungsten with a thickness of 50 nm or so. This scattering membrane mask is the mask used mainly for the electron-beam exposure method of scattering-angle limiting type (referred to as "SAL type" hereinafter) and the exposure method herein is assumed to be the SAL type.

Every division 100a is provided with one of segmented patterns which the pattern that is to be transferred onto a region 110a for one die on the substrate 110 is segmented into, and every segmented pattern is transferred onto the substrate 110, one by one. The external appearance of the substrate 110 is as shown in FIG. 6(b). A section (the Va section of FIG. 6(b)) of the substrate 110 is shown in FIG. 6(a) on an enlarged scale.

In FIG. 6, the z-axis is taken parallel to the optical axis AX of the optical system of charged particle beam, and the x-axis and y-axis are taken parallel to the directions of the array of divisions 100a, respectively. While the mask 100 and the substrate 110 are moved continuously in opposite directions along the x-axis as arrows Fm and Fw indicate, respectively, patterns of divisions 100a in one line are transferred in succession through step-by-step scanning of the charged particle beam in the direction of the y-axis. After completing projection of the patterns in one line, divisions 100a in the next of that line in the direction of the x-axis receive scanning of the charged particle beam. Thereafter, in the same manner, projection (segmented projection) of divisions. 100a is successively performed one by one so as to transfer the whole pattern for one die (chip).

The scanning order over the divisions 100a and the transcribing order onto the substrate 110 are presented by lines with arrowheads, Am and Aw, respectively. Hereat, the directions of movements for the mask 100 and the substrate 110 are opposite to each other, because the x-axis and y-axis for the mask 100 and the substrate 110 are reversed by a pair of projection lenses, respectively.

When the projection (segmented projection) is carried out in this manner, if patterns of divisions 100a in one line lying in the direction of the y-axis are projected on the substrate 110 by a pair of projection lenses as they are, gaps corresponding to the demarcation region 100b develop between regions for projection 110b on the substrate 110, each region for projection corresponding to a division 100a, respectively. To overcome this problem, the charged particle beam EB having passed through each division 110a is made deflected as much as the width Ly of the demarcation region 100b in the direction of the y-axis, whereby correction for the pattern projection position is made.

For the direction of the x-axis, besides moving the transmittable scattering mask 100 and the substrate 110 at respective specific speeds, in proportion to the ratio of pattern reduction, similar care is also taken. That is, when completing projection of divisions 100a in one line and turning to projection of divisions 100a in the next line, the charged particle beam EB is made deflected as much as the width Lx of the demarcation region 100b in the direction of the x-axis, whereby correction for the pattern projection position is made so as not to create a gap in the direction of the x-axis between regions for projection 110b.

As described above, in the segmented mask-pattern transfer type method, a mask onto which the whole segmented portions of the prescribed pattern of one chip are formed in all is used so that the throughput thereof can be markedly improved as compared with the conventional cell projection lithography method and the variable-shaped beam exposure method.

Further, in the segmented mask-pattern transfer type method, since a support structure in the form of a grid can be set over the demarcation region 100b which is formed between respective divisions 100a, bending and thermal distortion of the mask substrate which may result from irradiation of the charged particle beam can be suppressed well and exposure projection can be performed with high accuracy.

In the electron-beam exposure method of segmented mask-pattern transfer type described above, correction of the afore-mentioned proximity effect is still a matter of great importance.

As a proximity effect correction method for the electron-beam exposure method of segmented mask-pattern transfer type, G. P. Watson and others (J.Vac.Sci.Technol. B13(6), 2504–2507 (1995)) proposed a proximity effect correction method according to the SCALPEL (registered trademark) GHOST method in which the afore-mentioned GHOST is applied to the SAL type electron-beam exposure method.

The proximity effect correction method by G. P. Watson and others is described below.

With respect to a mask for this SAL type electron-beam exposure method, there is used a mask (referred to as a "scattering membrane mask", hereinafter) in which a apattern made of an electron-beam scatterer, for example, tungsten with a thickness of 50 nm or so, is formed on an electron-beam transmittable membrane (referred to simply as a "membrane", hereinafter) with a relatively small electron-beam scattering power, for example, a silicon nitride film with a thickness of 100 nm or so. The exposure is carried out over a wafer by an electron beam consisting of electrons which are not scattered or scattered only with relatively small scattering angles, having transmitted the membrane region where no scatterer is formed. Meanwhile, electrons scattered with large scattering angles, having transmitted the scatterer region, are cut off by a limiting aperture section disposed in the position or the vicinity of the cross-over. In this way, the image contrast is formed on the wafer through the difference of the electron-beam scattering between the membrane region and the scatterer region.

Although, in the mask in the above description of the segmented mask-pattern transfer type method, the demarcation region to partition prescribed patterns is in the form of a grid, it can be stripe-shaped and a mask used herein has actually a demarcation region formed in the shape of stripes. In the case that such a mask is utilized, the exposure of each division is carried out, while scanning electrically the inside of one zonal division partitioned by the stripe-shaped demarcation region, with the electron beam, in the direction of the length.

In the SAL type electron-beam exposure method as described above, the proximity effect correction is performed as follows. Firstly, some of electrons that are scattered by the scatterer on a scattering membrane mask are selectively allowed to pass through an annular opening which is set in a limiting aperture section disposed in the position or the vicinity of the cross-over, and then these scattered electrons allowed to pass are defocused to about the back-scattering range by spherical aberration of a projection lens and used as a correction exposure (GHOST exposure) beam to irradiate the wafer.

A schematic view of an optical system to explain the proximity effect correction in the SAL type method is shown in FIG. 7. Image-forming electrons passing through a mask 201 are focused by a first projection lens 202, and then pass through a central opening in a limiting aperture section 203, that is disposed in the cross-over plane or the back-focal plane, and subsequently form an image on a resist 206 on a wafer 205 by a second projection lens 204. The resist 206 in FIG. 7 is a negative one, of which an irradiated portion is to remain, and showing the form after development for illustration.

Meanwhile, most of electrons scattered by the mask 201 are blocked by the limiting aperture 203 and only a small part of the electrons pass through the central opening and an annular opening that surrounds the central opening. These mask-scattered electrons passed therethrough are defocused to about a back-scattering range $\beta b$ by the spherical aberration of the second projection lens 204, and distributed over the wafer as a correction exposure (GHOST exposure) beam. The central and the annular openings are concentrically disposed.

The intensity of the correction beam and, therefore, the correction dose that is proportional to the intensity is normally controlled by the area of the annular opening, and the range of defocusing, by the distance of the annular opening from the center of the limiting aperture or the radius of the opening. Since the opening area of the annular opening is larger than that of the central opening, the proximity effect correction, in practice, mostly depends on the scattered electrons passing through the annular opening. Further, in the actual design of a limiting aperture for exposure, as the back-scattering range largely depends on the wafer material and the accelerating voltage, under the same conditions of the wafer material and accelerating voltage, the position of an annular opening with respect to the center of the limiting aperture is set constant (the degree of defocusing is constant). Since the optimum correction dose depends on the substrate material, namely, the back-scattering coefficient $\eta$, the adjustment of the correction dose is made by changing the width of the annular opening (the opening area) according to the underlying substrate.

Next, referring to FIGS. 8 and 9, the basic principle of proximity effect correction in the afore-mentioned optical system shown in FIG. 7 is described.

FIG. 8(a) shows a scattering membrane mask, and referential numerals 301 and 302 indicate a membrane and a scatterer layer, respectively. FIG. 8(b) shows a distribution of energy deposition in the resist on the wafer when using a limiting aperture without an annular opening and providing no correction beam, in other words, when making no proximity effect correction, while FIG. 8(c) shows a distribution of energy deposition when using a limiting aperture with an annular opening and providing a correction beam, in other words, when making proximity effect correction. In the drawings, $\beta b$ is a back-scattering range. Assuming the energy of the forward-scattering electrons is 1, the back-scattering electrons have an energy corresponding to the back-scattering coefficient $\eta$, and the correction dose ration $\delta$ required in this instance is given by $\eta/(1+\eta)$. The energy of the back-scattering electrons can be obtained as the product of the pattern density and the back-scattering coefficient.

By defocusing the correction beam to about the back-scattering range $\beta b$ or L, the deposition energy, which has been lowered near the borderline, as seen in FIG. 8(b), can be brought to a constant level, as seen in FIG. 8(c). This results in an improvement of linewidth accuracy of the pattern.

In FIG. 9, the scattering membrane mask in FIG. 8(a) is replaced with a mask on which there is formed a line and space pattern (1/1), in other words, a pattern with a pattern density of 50%. As clearly seen in FIG. 9, even when the pattern density is changed, the proximity effect correction can be made in the same way.

However, the afore-mentioned proximity effect correction method for the SAL type electron-beam exposure method by G. P. Watson and others has a problem that regulation of the degree of defocusing and the amount of correction dose for correction exposure (GHOST exposure) is difficult.

The proximity effect correction method by G. P. Watson and others is a method in which the correction exposure is carried out concurrently with the pattern exposure and thereby the proximity effect correction is made. Because one exposure can accomplish both the pattern exposure and the proximity effect correction therein, this correction method has the advantage of a high throughput. Nevertheless, this method can only provide a high throughput and an excellent proximity effect correction when pattern projections are performed repeatedly, using one and the same mask and also applying electron-beam exposure to a substrate of the identical kind for exposure.

Apart from accelerating voltage, the degree of the proximity effect varies with the pattern density, the material of a substrate for exposure such as a wafer, the thickness of the resist film or the like. Therefore, when a mask having different patterns is utilized, when a substrate for exposure that is made of a different material is employed or when a resist layer is formed with a different thickness in any step of lithography, it is necessary to adjust the correction dose and the degree of defocusing in order to make the proximity effect correction appropriate to the particular mask, the substrate for exposure and the film thickness of the resist. Also when the thickness of the electron-beam scatterers varies with the mask, the scattering angles of the scattered electrons are changed and, accordingly, the correction dose is changed so that the correction dose must be adjusted all over again.

Because the adjustment of the correction dose is made by changing the radius and the width (the area) of the annular opening in the limiting aperture section 203, another limiting aperture section having a different annular opening must be in effect prepared separately. Moreover, to make exchange of the limiting aperture section, the electron-beam exposure must be suspended once and, relinquishing a vacuum condition, the inside of the optical system must be made open to the air beforehand. In short, the conventional method as described above has a problem that, if the optimum proximity effect correction suitable to the mask patterns and the substrate for exposure is to be achieved, a marked lowering of throughput must turn up.

Further, in practice, if the thickness of the scatterer layer formed over the membrane is varied within the mask plane in a fabricated scattering membrane mask, the scattering angles of electrons are changed in response to that. This alters the correction dose and makes the proximity effect correction insufficient. Consequently, in manufacturing a mask, uniformity of the highest standard is demanded for the film thickness throughout a mask plane but fabrication of a scattering membrane mask having such a highly uniform film thickness is not an easy task, resulting in a problem of lower yield and higher cost.

Further, apart from pattern density, within patterns for one chip or for a portion of several segments thereof, the extent of the proximity effect may vary with the underlying pattern. For example, when an underlying pattern of an interconnection or the like is formed of a heavy metal such as tungsten or the like on an underlying layer of the resist layer that is placed on the wafer surface, the incident electrons are reflected or back-scattered by that underlying pattern and, consequently, the extents of the proximity effect may become very much different between the resist region over the region where no underlying pattern is formed and the resist region over the underlying pattern formation region. In the afore-mentioned conventional correction method, correction exposure cannot be adjusted partially corresponding to the partially changed proximity effect within patterns for one chip or for a portion of several segments thereof.

SUMMARY OF THE INVENTION

An object of the present invention is to provide a method of electron-beam exposure wherein regulation of the correction exposure for the proximity effect correction can be made easily and excellent linewidth accuracy can be attained, and a mask as well as an electron-beam exposure system used therein.

The present invention relates to an electron-beam exposure method of segmented mask-pattern transfer type wherein a prescribed pattern is segmented into a plurality of divisions so as to form a segmented pattern in every said division and exposure is made through every said division one after another, whereby the projection of the whole of said prescribed pattern is accomplished; which comprises the steps of:

carrying out the exposure through every said division and transcribing a segmented pattern thereon one after another, and carrying out the correction exposure for every projection region of said segmented patterns one after another with a defocused beam of the inverse pattern of respective said segmented patterns, and thereby the proximity effect caused by the pattern exposure is corrected.

Further, the present invention relates to the electron-beam exposure method of segmented mask-pattern transfer type as set forth above; which comprises the steps of:

carrying out the exposure through every said division and transcribing a segmented pattern thereon one after another, while using a mask having, on one and the same substrate, a group of segmented patterns which are formed by segmenting the prescribed pattern into a plurality of divisions so as to form a segmented pattern in every said division and a group of inverse patterns of these segmented patterns; and carrying out the correction exposure for every projection region of said segmented patterns one after another with a defocused beam of the inverse pattern of respective said segmented patterns, and thereby the proximity effect caused by-the pattern exposure is corrected.

Further, the present invention relates to the electron-beam exposure method of segmented mask-pattern transfer type as set forth above; which comprises the steps of:

carrying out the exposure through every said division and transcribing a segmented pattern thereon one after another, while using a first mask having a group of segmented patterns which are formed by segmenting the prescribed pattern into a plurality of divisions so as to form a segmented pattern in every said division; and carrying out the correction exposure for every projection region of said segmented patterns one after another with a defocused beam of the inverse pattern of respective said segmented patterns, while using a second mask having a group of inverse patterns of said segmented patterns, and thereby the proximity effect caused by the pattern exposure is corrected.

Further, the present invention relates to the electron-beam exposure method of segmented mask-pattern transfer type as set forth above, wherein a stencil mask is used as the first mask and a scattering membrane mask is used as the second mask.

Further, the present invention relates to a mask for the electron-beam exposure that is used in the electron-beam exposure method as set forth above, which has, on one and the same substrate, a group of segmented patterns which are formed by segmenting the prescribed pattern into a plurality of divisions so as to form a segmented pattern in every said division and a group of inverse patterns of these segmented patterns.

Further, the present invention relates to an electron-beam exposure system having:

a structure which, with the mask as set forth above being disposed, can transfer said prescribed pattern by carrying out the exposure through the segmented pattern in every division one after another, and can apply the exposure to every projection region of the segmented pattern with the beam of the inverse pattern thereof by carrying out the exposure through the inverse pattern in every division one after another; and a structure which can defocus the beam of the inverse pattern every time the beam of the inverse pattern is used for exposure.

In the present invention, even when a mask is replaced with another one having different patterns or a substrate for exposure is changed with another one having a different back-scattering coefficient and then the electron-beam exposure is performed, the correction dose can be easily adjusted to the pattern density or the back-scattering coefficient thereat, by simply changing the irradiation time in carrying out the correction exposure through the inverse pattern in every division one after another. Further, when electron-beam exposure is performed with a substrate for exposure being replaced by another one made of a material having a different back-scattering range, the degree of defocusing can be adjusted to the back-scattering range by a dynamic focus lens in carrying out the correction exposure through the inverse pattern in every division one after another. In this way, the present invention can make the optimum proximity effect correction in accordance with the type of the mask and the substrate for exposure without lowering the throughput and, thus, can obtain an excellent linewidth accuracy.

Further, in the present invention, even within prescribed patterns for on chip or for a portion of several segments thereof, in carrying out the correction exposure through the inverse pattern in every division one after another, the correction dose can be locally regulated according to the locally varied proximity effect by adjusting the irradiation time of every shot to the extent of back-scattering which depends on the pattern density and the effects of the underlying pattern. Further, in the present invention, even within prescribed patterns for on chip or for a portion of several segments thereof, in carrying out the correction exposure through the inverse pattern in every division one after another, the degree of defocusing of the inverse pattern beam can be locally regulated according to the locally varied proximity effect by adjusting a dynamic focus lens for every shot to the effects of the underlying pattern which has a different back-scattering range from the one of the substrate.

In this way, the present invention can provide, within the prescribed pattern that is to be formed, the optimum correction exposures that vary with the location in response to the locally varied proximity effect, without lowering the throughput and, thus, can obtain excellent linewidth accuracy.

Further, the present invention can make the proximity effect correction using one and the same mask at any accelerating voltage, because the amount of blur of the correction exposure beam can be regulated by the dynamic focus lens, even if the back-scattering range changes with the accelerating voltage of the exposure system.

In the present invention, because both the primary patterns and inverse patterns are formed on the mask, no matter whether the resist employed is negative type or the positive type, excellent linewidth accuracy can be obtained by the same operations, using the same mask.

Further, in the present invention, the scattered electrons do not take part in the correction exposure so that uniformity of high standard is not required for the scatterer layer of the scattering membrane mask. As a result, the scattering membrane mask can be manufactured easily with low cost.

Further, in the present invention, since data for inverse pattern can be readily obtained, in manufacturing a mask, within a short time only by reversing tone of the pattern data in the CAD (Computer Aided Design) data, a lengthy data processing time that is hitherto required for the proximity effect correction can be drastically cut down. Further, when the positive patterns and the inverse patterns are formed on separate masks, if the negative resist and positive resist are employed for respective masks in fabricating masks, even the tone reversal of the pattern data described above becomes unnecessary. In this case, therefore, any data processing is not required for the proximity effect correction and, thus, pretreatment time for the proximity effect correction can be further reduced greatly.

Further, in the present invention, by employing a stencil mask and a scattering membrane mask as the masks for the prescribed pattern and the inverse pattern, respectively, masks can be fabricated easily without trouble even if patterns that may bring about the doughnut problem or leaf problem at the time of formation of inverse pattern are formed, and besides this makes possible to carry out the pattern exposure with high resolution.

DETAILED DESCRIPTION OF THE PREFERRED EMBODIMENTS

Figure 1:
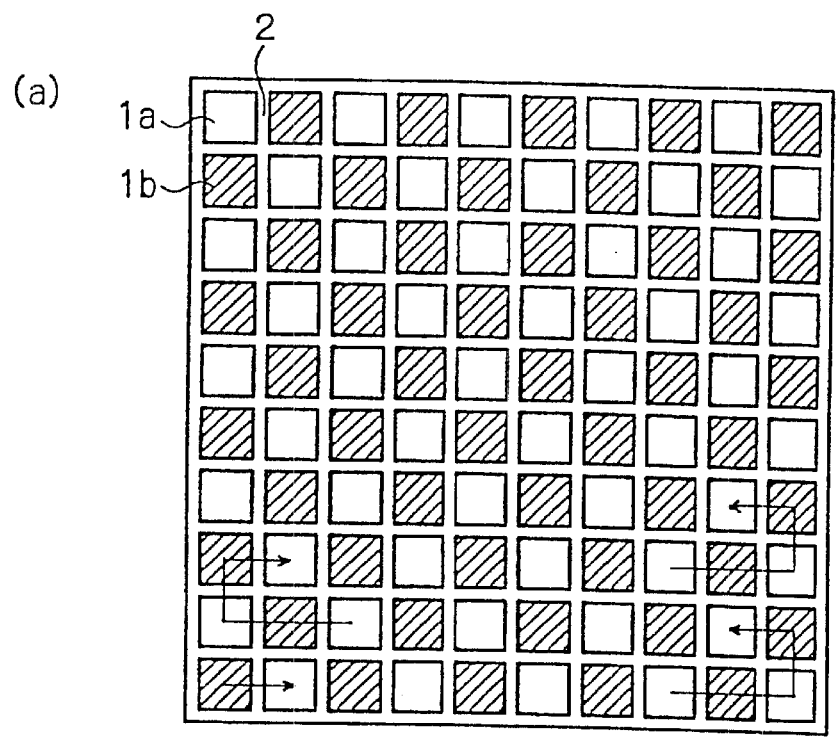
FIG. 1 is a schematic plan view in explaining the, composition of pattern region in a mask according to the present invention.
Figure 1:
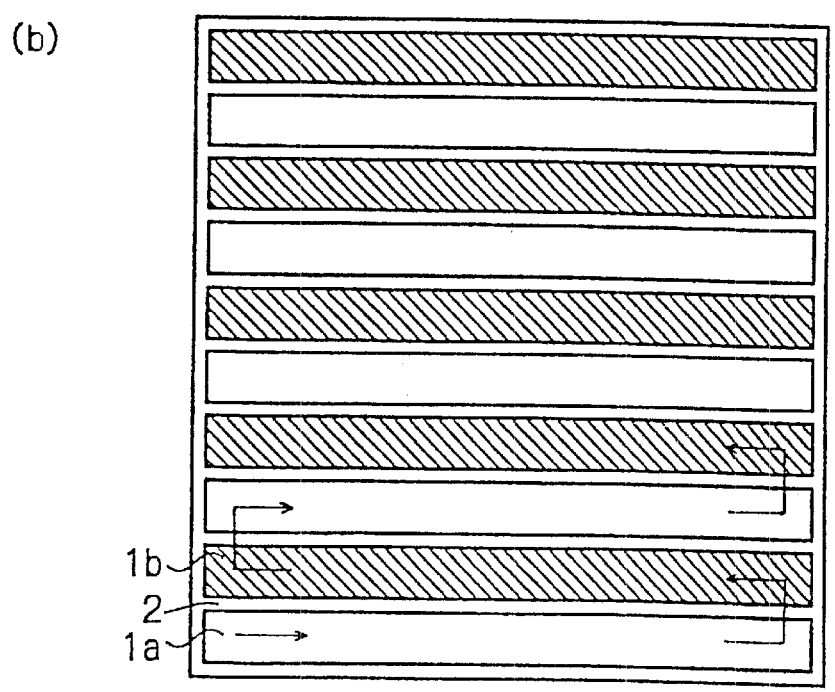

The preferred embodiments of the present invention are described below.

In the present invention, in an electron-beam exposure method of segmented mask-pattern transfer type wherein a prescribed pattern is segmented into a plurality of divisions and exposure is made through every one of these divisions one by one and thereby the whole of the prescribed pattern is transferred, for the purpose of making correction of the proximity effect cause by pattern exposure, the exposure through the segmented pattern in a division is carried out and thereafter the beam of correction exposure (GHOST exposure) which is formed by defocusing the beam of the inverse pattern of the segmented pattern is applied to a projection region for the segmented pattern in the division. The projection region for the segmented pattern as used herein indicates a region on the wafer that corresponds to a division on the mask through which exposure is made.

To apply the beam of correction exposure which is formed by defocusing the beam of the inverse pattern of a segmented pattern obtained by segmenting the prescribed pattern into a plurality of divisions to a projection region for the segmented pattern, there can be employed the following two techniques.

In the first technique, after exposure for one division at a time is made through one or more than one of segmented pattern(s), the beam of correction exposure formed by defocusing the beam of the inverse pattern of the segmented pattern is applied to a projection region for the segmented pattern at a time. By repeating these steps, projection of the whole of the prescribed pattern and correction exposure corresponding to that are accomplished in the end. As its embodiment, a mask having, on one and the same substrate, a group of segmented patterns which are formed by segmenting the prescribed pattern into a plurality of divisions in such a way that a segmented pattern is present in every one of these divisions and a group of inverse patterns of these segmented patterns are fabricated and, using this mask, the step of carrying out the exposure through one division at a time and transcribing the segmented pattern therein and the step of applying the beam of correction exposure formed by defocusing the beam of the inverse pattern of the segmented pattern to an projection region for the segmented pattern are performed by turns or in prescribed order.

In the second technique, a prescribed pattern is segmented into a plurality of divisions in such a way that a segmented pattern is present in every one of these divisions, and, by performing exposure through every division one by one, all segmented patterns are exposed and the whole of the prescribe pattern is transferred, and thereafter the beam of correction exposure formed by defocusing the beam of the inverse pattern of the segmented pattern is applied to every projection region for the segmented pattern one by one and the correction exposure for the whole of the prescribed pattern is in the end made. As an embodiment in which, after segmented projection of a prescribed pattern is completed, the correction exposure for the prescribed pattern is performed in parts, a first mask having a group of segmented patterns which are formed by segmenting the prescribed pattern into a plurality of divisions in such a way that a segmented pattern is present in every one of these divisions, and a second mask having a group of inverse patterns of these segmented patterns are fabricated, and after segmented projection of the prescribed pattern is made using the first mask, the beam of correction exposure formed by defocusing the beam of the inverse pattern of the segmented pattern is applied to every projection region for the segmented pattern that is formed with the first mask one by one, while using the second mask.

A mask used in the first technique is formed to have, on one and the same substrate, a group of segmented patterns which are formed by segmenting a prescribed pattern into a plurality of divisions in such a way that a segmented pattern is present in every one of these divisions and a group of inverse patterns of these segmented patterns. FIG. 1 is a schematic plan view in explaining the composition of a pattern region in a mask according to the present invention.

FIG. 1(a) is a view showing one example of composition in which a pattern region of the mask being segmented by a demarcation region 2 in the form of a grid, there are disposed square or rectangular divisions, while FIG. 1(b) is a view showing another example of composition wherein a pattern region of the mask being segmented by a demarcation region 2 in the form of stripes, there are disposed zonal divisions, parallel to each other. The lines with arrowheads in the drawing indicate the order of exposure for respective divisions on the mask.

While, in FIG. 1, the width of the demarcation region 2 is all the same, the width of one or more specific sections of demarcation region can be set wider for the sake of the mechanical strength of the mask. For example, in FIG. 1(a), by widening a central longitudinal and/or transverse line of the demarcation region, a plurality of divisions may be split into two or four groups of divisions within a mask. In this way, a plurality of divisions formed within one mask can be split into two or more groups of divisions forming distinct regions at intervals of any given length. In these demarcation regions, that is, regions where no pattern is formed, it is possible to set a supporting element or thicken the portion of the mask therein so that the mechanical strength of the mask can be increased. Such compositions of the mask can be similarly taken for a mask used in the second technique.

As an arrangement of divisions in the pattern region of the mask, for example, divisions of segmented pattern 1a and divisions of the inverse pattern thereof 1b can be laid alternately, as shown in FIG. 1(a). In electron-beam exposure using such a mask, the order of exposure through the segmented patterns and the inverse patterns thereof in respective divisions follow the arrangement of divisions in the mask and the exposure through the segmented pattern and the correction exposure with the beam formed by defocusing the beam of its inverse pattern are made alternately. The order of arrangement for divisions of respective segmented patterns 1a and divisions of the inverse patterns thereof 1b on the mask and the corresponding order of exposure are not limited to such 1:1 alternate array order as described above and the corresponding order of exposure, and the arrays can be arranged alternately in a preferable order and the exposure, according to that arrangement. For example, a mask wherein rows in each of which divisions 1a of segmented patterns are aligned and rows in each of which divisions 1b of inverse patterns thereof are aligned are laid in alternate order may be manufactured and, using this mask, the exposures through segmented patterns of all divisions 1a in one row and the correction exposures with the beam formed by defocusing the beam of the inverse patterns in all divisions 1b in the next row can be made alternately. Otherwise, a mask whose pattern region is divided into two sections, one section where only divisions 1a of segmented patterns are disposed and the other section where only divisions 1b of inverse patterns thereof are disposed may be manufactured and, using this mask, exposures through all segmented patterns on the mask may be first made and thereafter the beams of correction exposure formed by defocusing the beam of the inverse patterns of respective segmented patterns may be applied to corresponding projection regions for the segmented patterns one by one.

As another possible arrangement of divisions in the pattern region of the mask, there can be given the one shown in FIG. 1(b) in which zonal divisions of segmented pattern 1a and zonal divisions of the inverse pattern thereof 1b are laid alternately. Also in electron-beam exposure using such a mask, the order of projection for segmented patterns of respective divisions follows the arrangement of divisions in the mask and exposure through the segmented patterns and the a correction exposure with the beam formed by defocusing the beam of the inverse pattern thereof are made alternately line after line. Even in the case such zonal divisions are formed, the order of arrangement for divisions of respective segmented patterns 1a and divisions of the inverse patterns thereof 1b on the mask and the corresponding order of exposure are not limited to such 1:1 alternate line order as described above and the corresponding order of exposure, and the lines can be arranged alternately in a preferable order and the exposure, according to that arrangement. Otherwise, a mask whose pattern region is divided into two sections, one section where only divisions 1a of segmented patterns are disposed and the other section where only divisions 1b of inverse patterns thereof are disposed may be manufactured and, using this mask, exposures through all segmented patterns on the mask may be first made and thereafter the beams of correction exposure formed by defocusing the beam of the inverse patterns of respective segmented patterns may be applied to corresponding projection regions for the segmented patterns one by one.

Further, when the pattern region is partitioned in the form of a grid so as to form square or rectangular divisions as shown in FIG. 1(a), each division is formed to have a size possible to be exposed by one shot. As the exposure area by one shot of an electron-beam exposure system can be currently set to be 1 mm square or so, the size of the divisions on the mask can be also set to be, for example, 1 mm square or so. In this case, for example, through a ¼ reduction projection, projection to a region of 250 μm square on the wafer can be achieved by one shot. Meanwhile, when the pattern region is partitioned in the form of stripes so as to form zonal divisions as shown in FIG. 1(b), each division is formed to have a size that allows electrical scanning with the electron-beam in the direction of the length to expose the whole area within the division. For example, the width of the zonal divisions is set to be 1 mm and the length in the direction of the length is appropriately set according to the size of pattern region of the mask and the scanning width of the deflector.

The above description concerns the mask used in the first technique. In the second technique, a first mask having a group of segmented patterns (the positive patterns) which are formed by segmenting a prescribed pattern into a plurality of divisions in such a way that a segmented pattern is present in every one of these divisions and a second mask having a group of inverse patterns of these segmented patterns are used as a combination.

For the first mask having a group of segmented patterns that are positive patterns, well-known masks used in the conventional electron-beam exposure method of segmented mask-pattern transfer type can be employed. The second mask having a group of inverse patterns can be formed by forming a structure wherein inverse patterns are respectively disposed at positions corresponding to the formation positions of segmented patterns in the first mask. In other words, the mask can be fabricated by segmenting the inverse pattern of the prescribed pattern that is to be formed into a plurality of divisions in such a way that all the segmented inverse patterns are formed at positions corresponding to respective segmented patterns in the first mask.

The "prescribed pattern" used in the above description indicates a positive pattern corresponding to the pattern for one chip or a portion of several segments thereof and is a positive pattern that is to be formed by projection through one mask. It is preferable to use a mask in which a positive pattern that is to be formed for one chip is all formed, but, if necessary, the positive pattern for one chip can be segmented into several segments and respective masks may be fabricated and used for these several segmented patterns. Normally, it is segmented into 2 to 3. For example, when the positive pattern for one chip is segmented into 2, respective masks are fabricated for these two segmented patterns and the positive pattern for one chip is formed using two masks.

All positive and inverse patterns for one chip might be formed on one mask. Nevertheless, if the positive pattern for one chip is segmented as described above, in the first technique, the positive pattern that is to be formed on one chip is made, in masks of the same number as the number of segmentation. The positive patterns (the prescribed patternrs) that are allocated to respective masks are further divided into a plurality of divisions within respective masks. Each mask is manufactured to have, on one and the same substrate, a group of segmented patterns that are formed in one of these divisions and a group of inverse patterns of every one of these segmented patterns. Meanwhile, in the second technique, the primary positive pattern that is to be formed on one chip is segmented to several patterns and the positive patterns (the prescribed patterns) that are allocated to respective masks are further divided into a plurality of divisions within respective masks. A group of segmented patterns that are each formed in one of these divisions are formed on a mask substrate. In effect, first masks of the same number as the number of segmentation are formed. Further, according to every one of first masks, a group of inverse patterns are formed on a mask substrate for every one of segmented patterns as described above and thereby a second mask is formed. Although the second masks are, in general, fabricated as many as the first masks, one or more masks the number of which may be different from the number of the first masks might be fabricated. Further, while it is possible to fabricate masks in each of which a group of segmented patterns and a group of inverse patterns described above are formed on one and the same mask substrate, with such masks being used, the pattern exposure should be carried out by the first technique.

The mask used in the present invention can be fabricated by forming the segmented patterns or their inverse patterns in respective divisions as described above in the mask structure of the type that is generally used in the electron-beam exposure method of segmented mask-pattern transfer type. Or, in the second technique wherein the positive patterns and the inverse patterns are formed on separate masks, if two different tones of resist, that is, the negative one and the positive one are employed for respective patterns, the inverse patterns can be formed easily without reversing the CAD data.

The inverse patterns that are each formed in one of divisions of the mask used in the present invention can be formed easily by reversing the CAD data used for forming their corresponding segmented patterns. Therefore, complicated calculations are unnecessary so that masks can be manufactured in a short time. Moreover, because the inverse patterns are formed each in one of divisions of the mask, in making the correction exposure with these inverse patterns, the correction exposure can be applied from division to division by one shot or one scan and, thus, the correction exposure can be completed within a short time.

As for the type of a mask that can be employed to the present invention, a scattering membrane mask and a stencil mask can be given.

Firstly, a scattering membrane mask is described. A scattering membrane mask is a mask in which a pattern made of an electron-beam scatterer is formed on an electron-beam transmittable membrane (referred to as a "membrane" hereinafter) with a relatively small electron-beam scattering power, as described above. The exposure is carried out over a wafer by an electron beam consisting of electrons which are not scattered or scattered only with relatively small scattering angles, having transmitted the membrane region where no scatterer is formed. Meanwhile, scattered electrons having transmitted the scatterer region are cut off by a limiting aperture section disposed in the position or the vicinity of the cross-over. Alternatively, the scattered angles are set large by selecting an appropriate thickness of the scatterer or the like and the scattered electrons are.prevented from irradiating the wafer. In this way, the image contrast is formed on the wafer through the difference of the electron-beam scattering between the membrane region and the scatterer region.

For the membrane, a silicon nitride film with a thickness of 50 to 150 nm can be used. As a scatterer, a tungsten (W) layer or a W/C layered film with a thickness of 50 nm or so can be formed over the membrane and then patterned. Other scatterer layer materials possible to use include heavy metals such as chromium, molybdenum, titanium, gold and platinum and polycrystal materials such as polysilicon, tungsten silicide, molybdenum silicide, titanium silicide and the like.

A description of a manufacturing method of a scattering membrane mask can be found, for example, in SPIE, Vol. 3236, pp. 190 (1998). An example of a manufacturing method of a scattering membrane mask is described below.

First, upon a silicon substrate, silicon nitride films are formed as electron-beam transmittable thin films (membranes) by the LPCVD (Low Pressure Chemical Vapour Deposition) method. The silicon nitride films are, hereat, formed on the both surfaces of the silicon substrate. Subsequently, over the silicon nitride film formed on the surface of the substrate, a tungsten layer is grown by means of the sputtering as a scatterer layer.

Next, over the silicon nitride film formed on the backside of the silicon substrate, a coating of a resist is applied and patterned, and using the formed resist pattern as a mask, the silicon nitride film is removed by reactive ion etching so as to expose the silicon substrate in a prescribed region. Further, after this, step, a tungsten layer may be formed over the silicon nitride film on the top surface of the substrate.

After the removal of the resist, by carrying out wet-etching with KOH, silicon in the exposed region of the silicon substrate is removed and thereby an opening section to expose the silicon nitride film formed on the top surface of the substrate is formed.

Subsequently, over the tungsten layer lying on the top side of the substrate, a coating of a resist is applied and patterned, and using the formed resist pattern as a mask, the tungsten layer is patterned by dry etching. By removing the resist, a scattering membrane mask in which a tungsten layer pattern is formed on the silicon nitride film is obtained.

Next, a stencil mask is described. As a stencil mask, there is generally used a mask in which an opening pattern is formed in a substrate that does not allow the electron beam to transmit at a given accelerating voltage, for instance, a silicon substrate with a thickness of not less than 20 $\mu$m when the accelerating voltage is 50 kV. While the electron beam passing through the opening that is patterned arrives on the wafer as image-forming electrons, the non-opening section of the silicon mask substrate blocks the electron beam through absorption or reflection. Accordingly, when a stencil mask is utilized, an image contrast is formed on the wafer by the so-called absorbing contrast. Further, considering the prevention of the heat generation in the mask that may be caused by the absorption of electron beam and the improvement in accuracy of formation of the opening pattern, it is possible to make the mask substrate thin enough to allow the electron beam to transmit the non-opening section. Only in this case, it is necessary to take measures. For example, a limiting aperture may be introduced within the optical system of the electron-beam exposure system so as to cut off the scattered electrons having transmitted the non-opening section of the mask substrate, or scatterers are laid on the non-scattered section of the mask to make the scattered angles of transmitting electrons larger so that the scattered electrons, having transmitted, may not fall on the wafer or lower the contrast. Accordingly, in the case of a stencil mask (a scattering stencil mask) wherein an opening pattern is formed in a mask substrate region that is sufficiently thin to allow the electron beam to transmit, pattern formation is mainly made by the scattering contrast. Especially when a silicon substrate is utilized therein, as the thickness of the mask substrate becomes less and the transmission thereof increases, the pattern formation becomes more and more dependent on the scattering contrast and, in the end, becomes almost solely dependent on that. For example, when an accelerating voltage is set to be 100 kV, if the thickness of the pattern formation region of a silicon substrate is set to be not less than 0.2 $\mu$m but not greater than 5 $\mu$m, and more preferably not less than 0.3 $\mu$m but not greater than 3 $\mu$m, the pattern formation with a stencil mask can be obtained through the scattering contrast.

For the stencil mask, there is known a problem that a mask may be easily damaged when a mask has a pattern, for example, comprising bar-shaped patterns disposed to form all four sides or only three sides of a rectangle or a square. Because a section that supports the region surrounded by bar-shaped patterns and its adjacent region (for example, four corner sections for a square pattern) in such a mask, for example, occupies only an limited area and has a low strength, the mask may be easily damaged at the supporting section, while being handled. Also a closed pattern composed of bar-shaped patterns is bound to fall off, losing thoroughly the supporting section. The problem of this sort, which is sometimes called the doughnut problem or the leaf problem, may arise when the inverse patterns are formed on the mask substrate, as well.

Accordingly, in the present invention, to overcome these problems, in regard of segmented patterns and inverse patterns that may bring about these particular problems, those segmented patterns and inverse patterns that are each formed originally in one of divisions are further segmented into several patterns and these respective patterns are set in one of divisions on the mask so as not to lose their supporting sections or weaken the mechanical strength of their supporting sections. For example, when a segmented pattern formed in one division is further segmented to form two segmented patterns, these new segmented patterns are set separately in two divisions. The divisions in which these newly segmented patterns are each set are preferably placed next or near to one another, for the sake of the writing accuracy.

Figure 2:
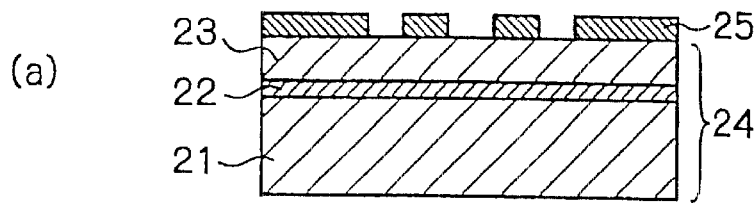
FIG. 2 is a series of cross-sectional views illustrating the steps of one example of a method of manufacturing a mask according to the present invention.
Figure 2:
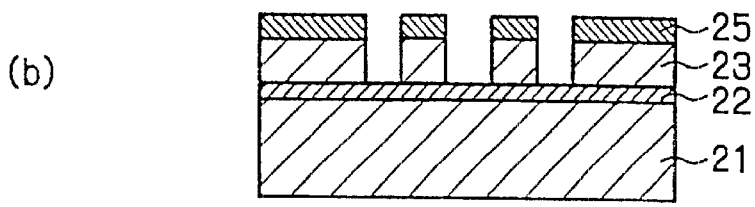
Figure 2:
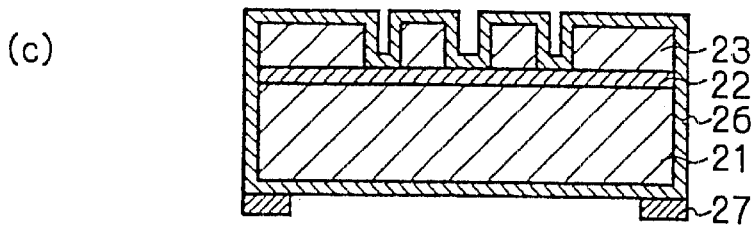
Figure 2:
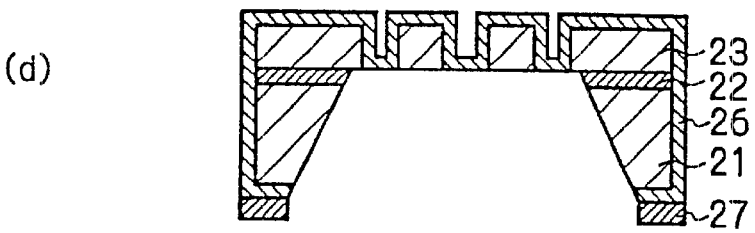
Figure 2:
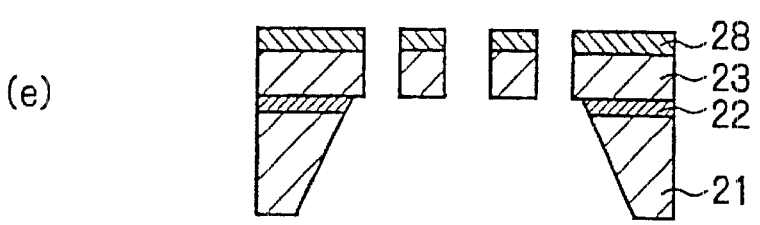

Next, referring to FIG. 2, one example of a manufacturing method of a stencil mask is described.

First, on a composite wafer 24 (Si/SiO$_2$/Si), a resist layer is formed and then patterned by lithography, as shown in FIG. 2(a), where referential numerals 21 and 23 represent Si layers and 22, a SiO$_2$ layer.

Next, as shown in FIG. 2(b), using a patterned resist layer 25 as a mask, the Si layer 23 is dry-etched.

After removing the resist layer, a silicon nitride film 26 is then formed as a protective film for wet-etching that is to be performed in the later step, as shown in FIG. 2(c). Next, on the backside, a resist layer is formed and then patterned to form a resist layer 27 with an opening window in the center thereof.

Next, as shown in FIG. 2(d), the Si layer 21 exposed in the opening section is wet-etched by an alkaline solution such as a potassium hydroxide solution. The tapered shape of the Si layer 21 is formed, making use of the orientation of the Si layer. Subsequently, using hydrofluoric acid, the exposed SiO$_2$ film 22 is removed by means of wet etching.

After that, as shown in FIG. 2(e), the resist layer 27 and the protective film 26 are removed, and a conductive film 28 made of, for example, gold, platinum or palladium is formed over the surface by the sputtering method or the like.

As the scattering membrane mask and the stencil mask described above have their own advantageous characteristics, it is preferable to choose the appropriate mask to the conditions of the step of lithography or use as a combination. When a combination of these two masks are utilized, it is possible to employ a stencil mask as the first mask to form prescribed patterns (the positive patterns) and a scattering membrane mask, as the second mask to form inverse patterns, or alternatively a scattering membrane mask as the first mask and a stencil mask as the second mask.

The scattering membrane mask does not have the doughnut problem or the leaf problem that is a problem specific to the stencil mask, although its resolution becomes lowered due to chromatic aberration because image-forming electrons lose their energy through inelastic scattering in the membrane, transmitting the membrane region. Certainly, the stencil mask can attain a higher resolution than the scattering membrane mask. In view of these factors, it is preferable that a stencil mask is employed as the first mask to form prescribed patterns (positive patterns) and a scattering membrane mask, as the second mask to form inverse patterns. By using a stencil mask as the first mask to form prescribed patterns, a higher resolution can be obtained, in comparison with the case that a scattering membrane mask is employed for that. Further, by selecting a scattering membrane mask as the second mask to form inverse patterns, an inverse pattern mask can be readily fabricated without trouble even if patterns that are liable to cause the doughnut problem or leaf problem at the time of formation of inverse patterns are formed.

Figure 3:
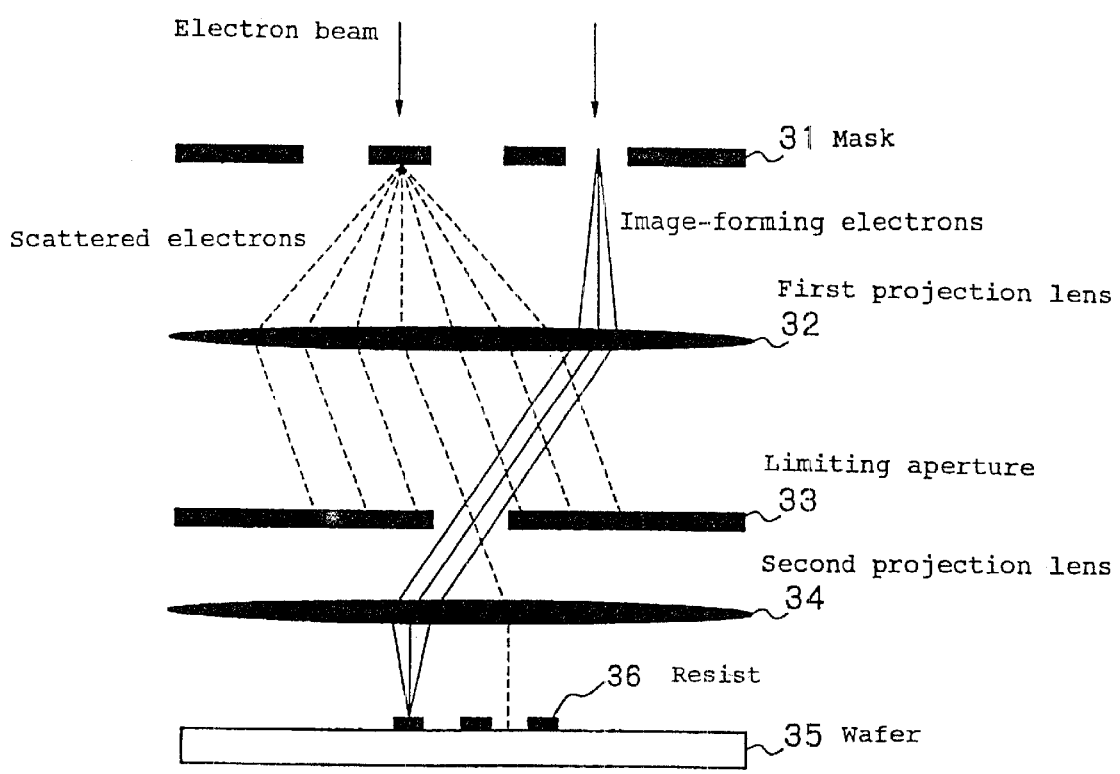
FIG. 3 is a schematic diagram in explaining the optical system in an electron-beamzexposure system according to the present invention.
Figure 4:
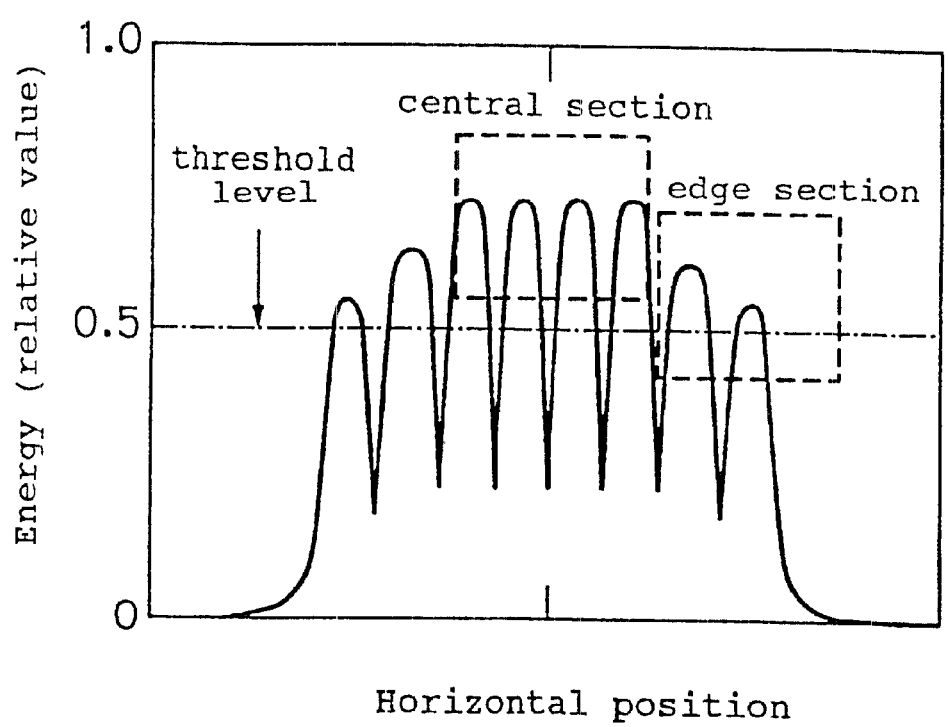
FIG. 4 is a diagram showing the distribution of deposited energy brought about by the electron-beam exposure in explaining the proximity effect.
Figure 5:
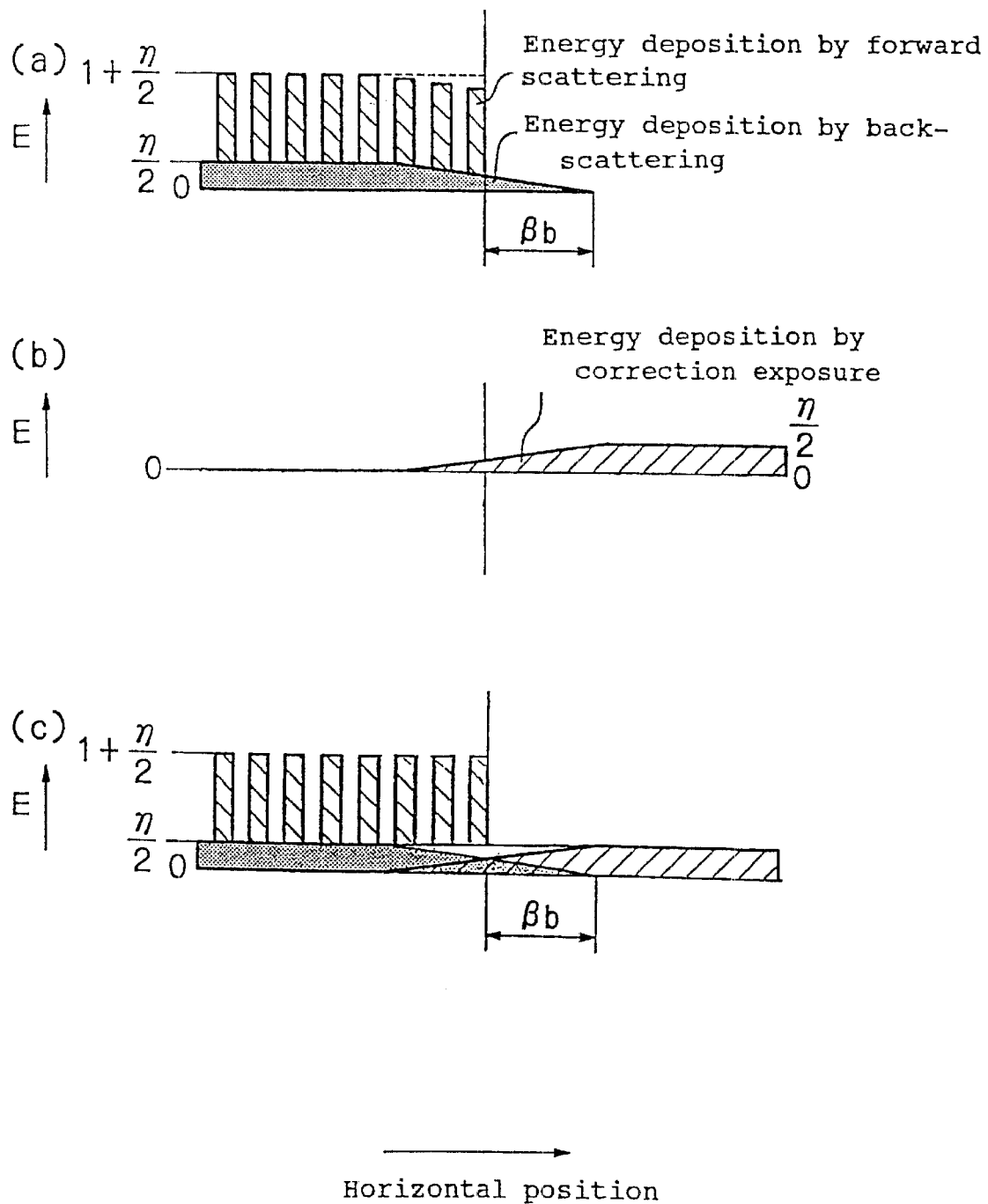
FIG. 5 is a schematic diagram in explaining the principle of proximity effect correction according to the GHOST method.
Figure 6:
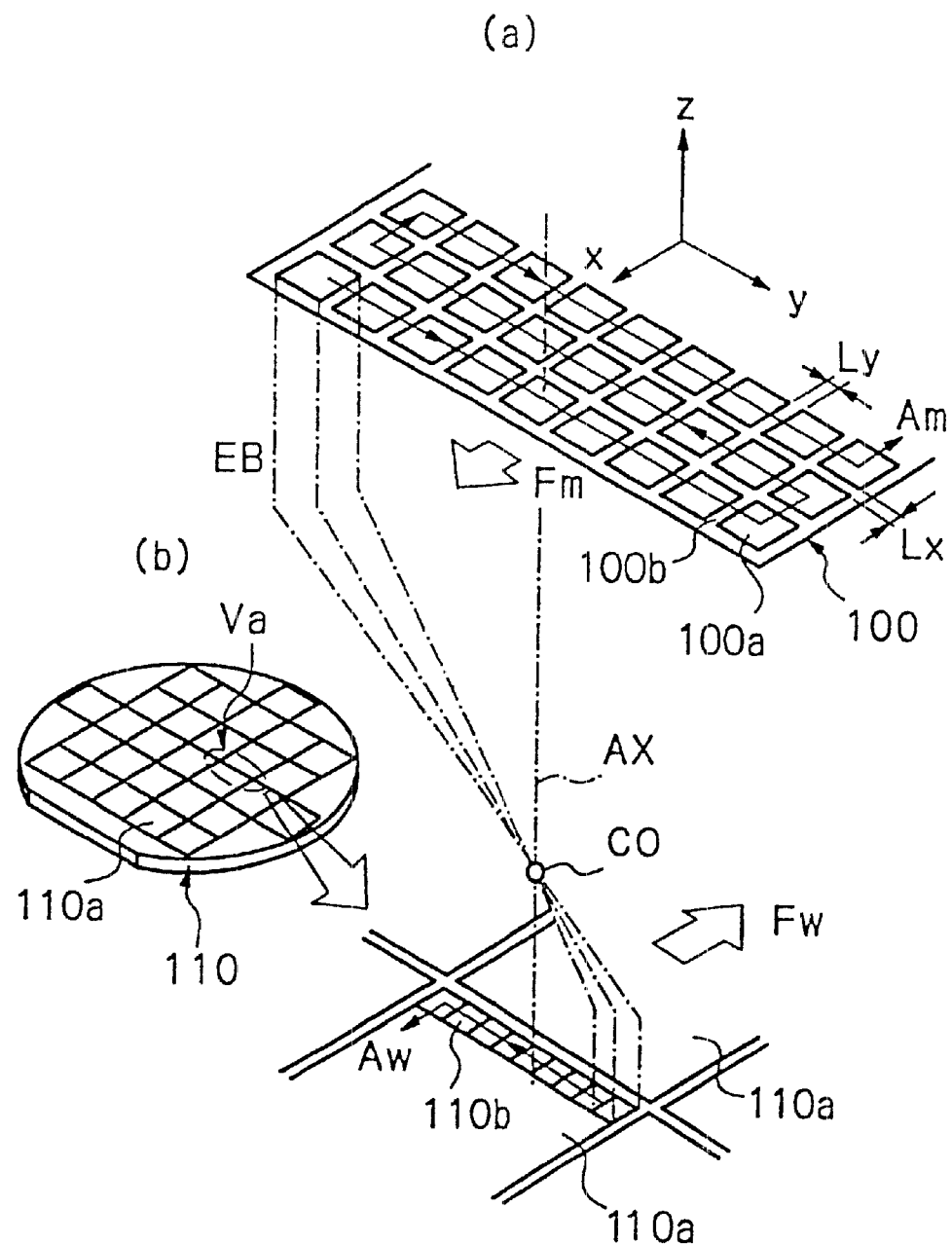
FIG. 6 is a schematic view in explaining an electron-beam exposure method of segmented mask-pattern transfer type.
Figure 7:
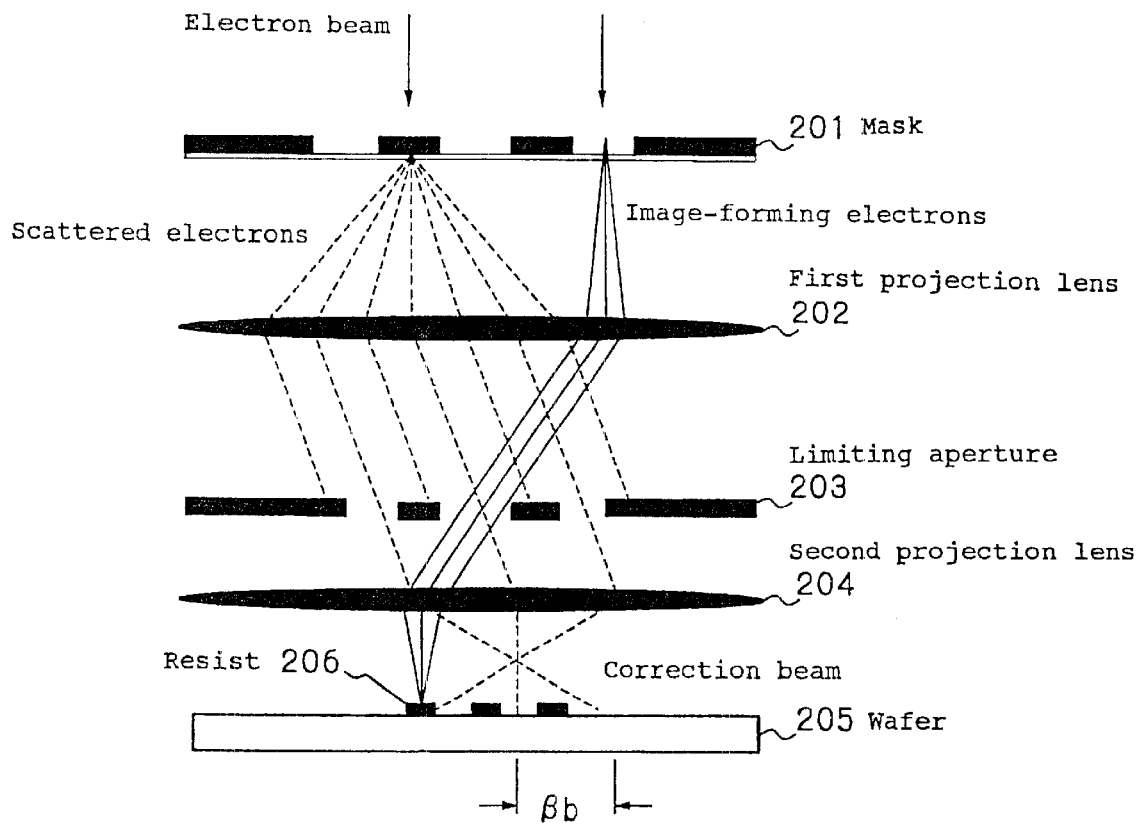
FIG. 7 is a schematic diagram of the optical system in explaining the conventional proximity effect correction in an electron-beam exposure method of scattering-angle limiting type.
Figure 8:
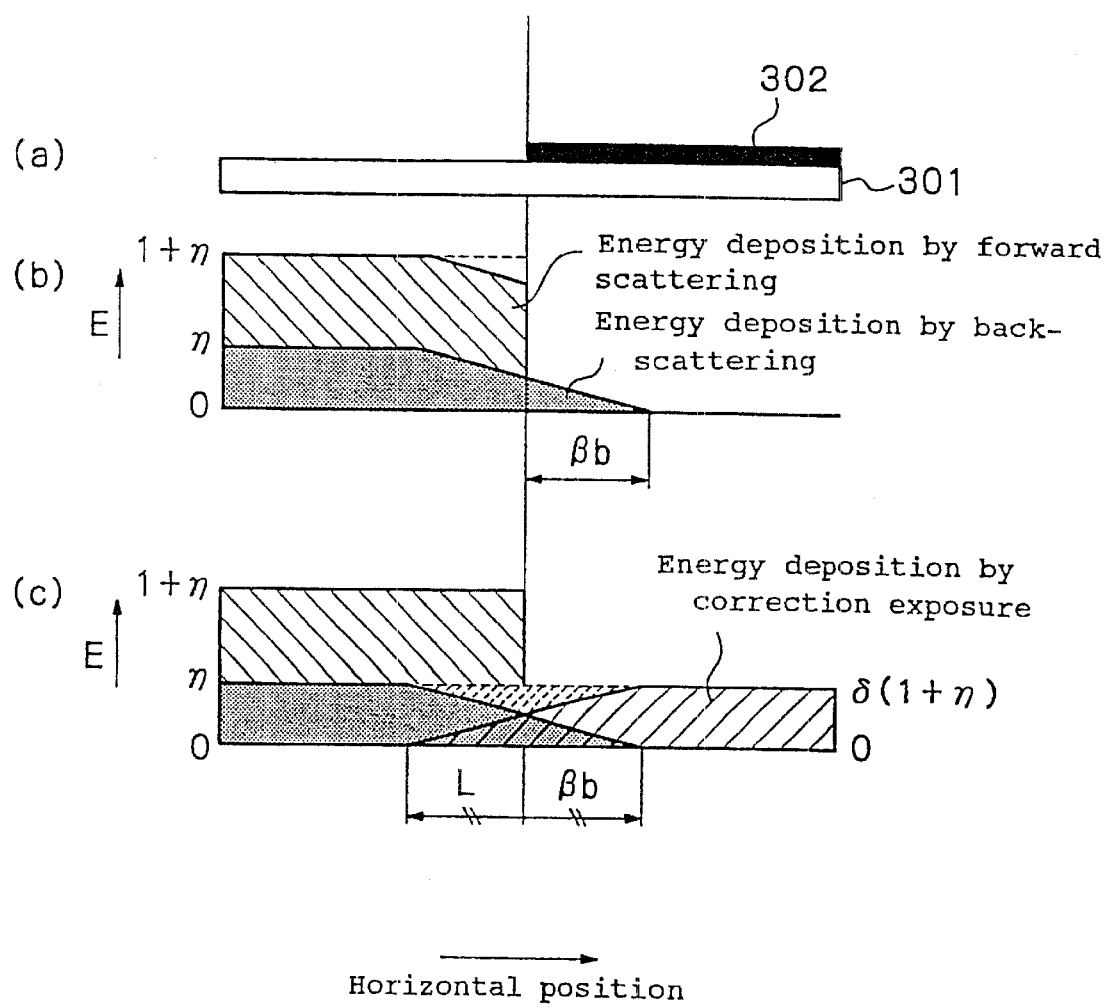
FIG. 8 is a diagram in explaining the principle of the conventional proximity effect correction in an electron-beam exposure method of scattering-angle limiting type.
Figure 9:
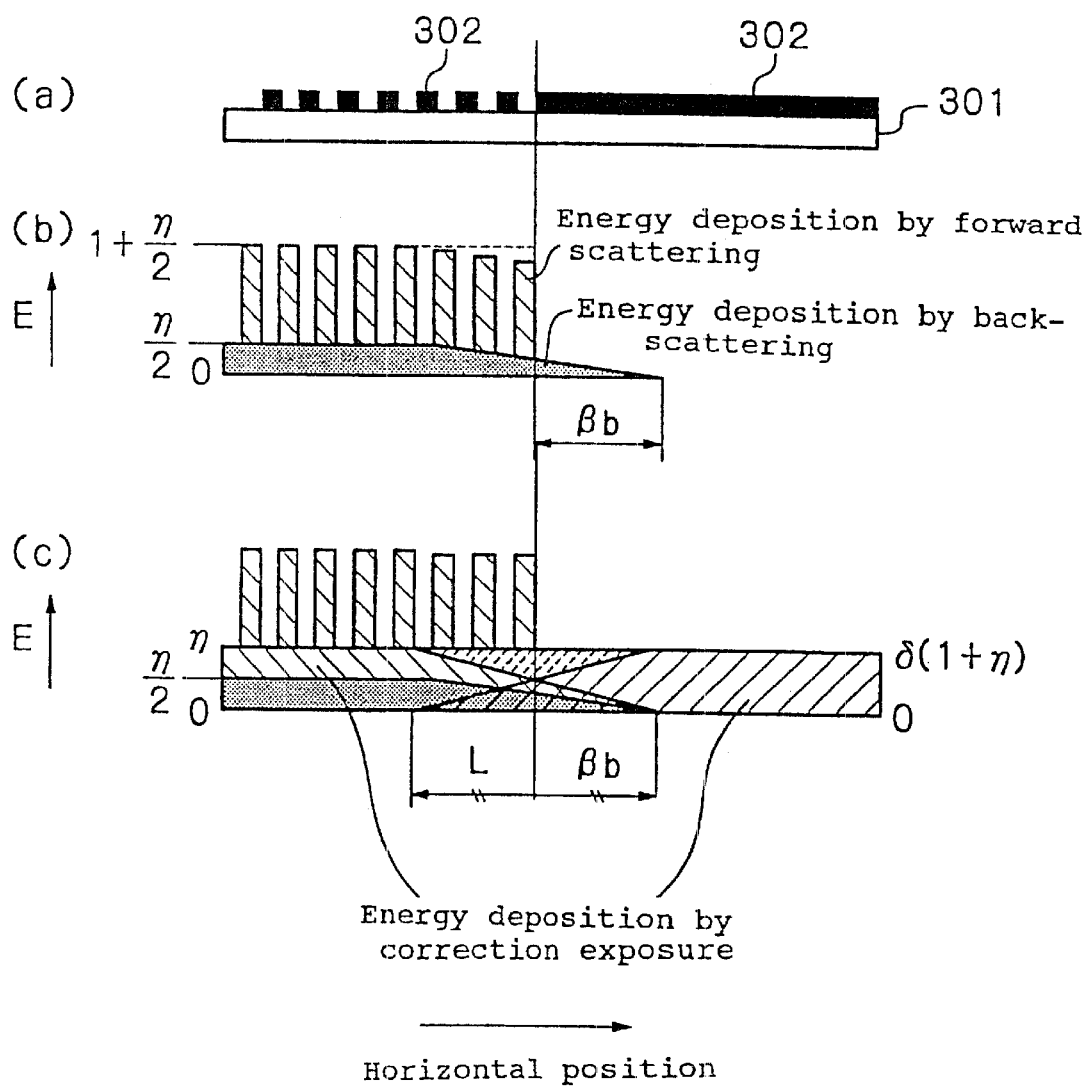
FIG. 9 is a diagram in explaining the principle of the conventional proximity effect correction in an electron-beam exposure method of scattering-angle limiting type.

Next, referring to FIG. 3, an electron-beam exposure system used for the present invention is described.

FIG. 3 is a schematic diagram of an optical system in which a scattering membrane mask is employed as a mask 31. An opening region and a non-opening region of the mask 31 correspond to a membrane region and a scatterer region of a scattering membrane mask, respectively.

After scattered electrons that have transmitted the mask pass through a first projection lens 32, they are almost completely blocked by a limiting aperture section 33 disposed in the position or the vicinity of the cross-over plane (the back-focal plane). If the scattering angles of the scattered electrons are so large that the scattered electrons hardly fall on the wafer 35 or if the substrate of the stencil mask is thick enough to block the electron-beam, the limiting aperture section 33 is not necessarily required to obtain the contrast.

Against the afore-mentioned scattered electrons, image-forming electrons passing through either an opening section of a prescribed pattern mask (a stencil mask) or a membrane region of a mask (a scattering membrane mask) are focused by the first projection lens 32, and then pass through a central opening in the limiting aperture section 33 and, subsequently, by a second projection lens 34, are made to form an image on a resist 36 laid on a wafer 35. The resist 36 shown in FIG. 3 is a negative one of which an irradiated portion is to remain, and in the form after development for illustration. The resist may be a positive one. The first and the second projection lenses hereat constitute doublet optics.

Meanwhile, image-forming electrons passing through an opening section or a membrane region of an inverse pattern mask are focused by the first projection lens 32, and then pass through the central opening in the limiting aperture section 33. Subsequently, along with forming an image by passing through the second projection lens 34, these electrons are defocused to about a back-scattering range by a dynamic focus lens (not shown in the drawing) that is disposed in the same position as or in the vicinity of the second projection lens 34 and distributed over the wafer as a correction beam.

The dynamic focus lens mechanism is generally set for the purpose of adjusting the focus plane to the height of the wafer or making correction after the change of the focus due to the Coulomb effect takes place. In the present invention, while the mechanism serves to make normal operations at the time of exposure for the positive patterns, it controls the focus position at the time of exposure for the inverse patterns so that the inverse pattern beam may be defocused to about the back-scattering range. Further, since the degree of the blur of the inverse pattern beam can be regulated through an adjustment of the operating conditions (the focus position) of the dynamic focus lens, when a wafer is replaced by another one made of a material with a different back-scattering range or when the back-scattering range within one wafer varies with location depending on the presence of the underlying pattern that is made of a material with a different back-scattering range from the one of the substrate, the degree of blur can be regulated for every individual wafer or region.

Further, by the irradiation time of the defocused inverse pattern beam, the correction dose can be controlled according to the conditions of the substrate for exposure.

What is claimed is:

1. An electron-beam exposure method of segmented mask-pattern transfer type, comprising the steps of:
    segmenting a prescribed pattern into a plurality of divisions so as to form a segmented pattern in every said division;
    exposing every said division one after another, and transcribing said segmented pattern thereon one after another, whereby the projection of the whole of said prescribed pattern is accomplished; and
    carrying out the correction exposure for every projection region of said segmented patterns one after another with a defocused beam of the inverse pattern of respective said segmented patterns, and thereby the proximity effect caused by the pattern exposure is corrected.

2. The electron-beam exposure method of segmented mask-pattern transfer type according to claim 1; which comprises the steps of:
    carrying out the exposure through every said division and transcribing a segmented pattern thereon one after another, while using a mask having, on one and the same substrate, a group of segmented patterns which are formed by segmenting the prescribed pattern into a plurality of divisions so as to form a segmented pattern in every said division and a group of inverse patterns of these segmented patterns; and
    carrying out the correction exposure for every projection region of said segmented patterns one after another with a defocused beam of the inverse pattern of respective said segmented patterns, and thereby the proximity effect caused by the pattern exposure is corrected.

3. The electron-beam exposure method of segmented mask-pattern transfer type according to claim 1; which comprises the steps of:
    carrying out the exposure through every said division and transcribing a segmented pattern thereon one after another, while using a first mask having a group of segmented patterns which are formed by segmenting the prescribed pattern into a plurality of divisions so as to form a segmented pattern in every said division; and
    carrying out the correction exposure for every projection region of said segmented patterns one after another with a defocused beam of the inverse pattern of respective said segmented patterns, while using a second mask having a group of inverse patterns of said segmented patterns, and thereby the proximity effect caused by the pattern exposure is corrected.

4. The electron-beam exposure method of segmented mask-pattern transfer type according to claim 3, wherein a stencil mask is used as the first mask and a scattering membrane mask is used as the second mask.

5. A mask for the electron-beam exposure that is used in the electron-beam exposure method according to claim 2, which has, on one and the same substrate, a group of segmented patterns which are formed by segmenting the prescribed pattern into a plurality of divisions so as to form a segmented pattern in every said division and a group of inverse patterns of these segmented patterns.

6. An electron-beam exposure system having:
    a structure which, with the mask according to claim 5 being disposed, can transfer said prescribed pattern by carrying out the exposure through the segmented pattern in every division one after another, and can apply the exposure to every projection region of the segmented pattern with the beam of the inverse pattern thereof by carrying out the exposure through the inverse pattern in every division one after another; and
    a structure which can defocus the beam of the inverse pattern every time the beam of the inverse pattern is used for exposure.

* * * * *